United States Patent
Igel et al.

(10) Patent No.: US 6,434,424 B1
(45) Date of Patent: Aug. 13, 2002

(54) REGULARIZATION OF VENTRICULAR RATE DURING ATRIAL TACHYARRHYTHMIA

(75) Inventors: David A. Igel, Lino Lakes; H. Toby Markowitz, Roseville; Robert A. Betzold, Fridley; Karen J. Kleckner, New Brighton; Jeremy A. Schroetter, Lauderdale, all of MN (US)

(73) Assignee: Medtronic, Inc., Minneapolis, MN (US)

( * ) Notice: Subject to any disclaimer, the term of this patent is extended or adjusted under 35 U.S.C. 154(b) by 0 days.

(21) Appl. No.: 09/470,120

(22) Filed: Dec. 22, 1999

Related U.S. Application Data (60) Provisional application No. 60/113,988, filed on Dec. 28, 1998.

(51) Int. Cl.$^7$ .............................................. A61N 1/362
(52) U.S. Cl. ............................................................ 607/9
(58) Field of Search .............................. 607/4, 5, 9, 14

(56) References Cited

U.S. PATENT DOCUMENTS

| | | | |
|---|---|---|---|
| 4,539,991 A | 9/1985 | Boute et al. | 128/419 PG |
| 4,686,989 A | 8/1987 | Smyth et al. | 128/419 PG |
| 4,890,617 A | 1/1990 | Markowitz et al. | 128/419 PG |
| 4,932,406 A | 6/1990 | Berkovits | 128/419 PG |
| 4,941,471 A | 7/1990 | Mehra | 128/419 PG |
| 4,944,298 A | 7/1990 | Sholder | 128/419 PG |
| 4,951,667 A | 8/1990 | Markowitz et al. | 128/419 PG |
| 5,144,949 A | 9/1992 | Olson | 128/419 PG |
| 5,273,035 A | 12/1993 | Markowitz et al. | 607/14 |
| 5,282,836 A * | 2/1994 | Kreyenhagen et al. | 607/14 |
| 5,282,839 A | 2/1994 | Roline et al. | 607/19 |
| 5,292,340 A | 3/1994 | Crosby | 607/17 |

(List continued on next page.)

OTHER PUBLICATIONS

R. J. Cohen et al., "Quantitative Model for Ventricular Response During Atrial Fibrillation", *IEEE Transactions on Biomedical Engineering* vol. 30, pp. 769–782 (1983).

Wittkampf et. al., "Rate Stabilization by Right Ventricular Pacing in Patients With Atrial Fibrillation", *PACE*, vol. 9, Nov.–Dec., 1986, Part II, pp. 1147–1153.

Wittkampf et. al., "Effect Of Right Ventricular Pacing On Ventricular Rhythm During Atrial Fibrillation", *JACC* 11:539–545, (1988).

Lau et al., "A New Pacing Method for Rapid Regularization and Rate Control in Atrial Fibrillation", *Am Journal of Cardiology*, vol. 65, pp. 1198–1203, May 15, 1990.

*Primary Examiner*—George R. Evanisko
(74) *Attorney, Agent, or Firm*—Girma Wolde-Michael (57) ABSTRACT

A pacing system provided with a mode switching feature and ventricular rate regularization (VRR) function adapted to stabilize or regularize ventricular heart rate during chronic or paroxysmal atrial tachyarrhythmia. In a preferred embodiment, the pacing system nominally operates in an atrial synchronized pacing mode such as DDD or DDDR pacing mode. In response to detection of atrial rhythm characteristics consistent with an atrial tachyarrhythmia, e.g., atrial fibrillation, a mode switch into a non-atrial synchronized, ventricular rate regularization pacing mode, e.g. DDIR or VDIR pacing mode, is made. If the VRR function is programmed on, the ventricular pacing rate based upon a rate responsive sensor derived ventricular pacing rate modulated on a beat by beat basis by preceding intrinsic or paced ventricular events, the stability of the intrinsic ventricular heart rate, and any atrial pace events to regularize the ventricular pacing rate. The pacing system may also be permanently programmed to the DDIR pacing mode with the VRR feature functioning continuously. The pacing system may also be permanently programmed to the VVIR pacing mode with VRR function activated, but without consideration of atrial pace events.

20 Claims, 6 Drawing Sheets

U.S. PATENT DOCUMENTS

| | | | |
|---|---|---|---|
| 5,318,594 A | 6/1994 | Limousin et al. | 607/9 |
| 5,480,413 A * | 1/1996 | Greenhut et al. | 607/14 |
| 5,522,859 A | 6/1996 | Stroebel et al. | 607/19 |
| 5,545,186 A | 8/1996 | Olson et al. | 607/14 |
| 5,562,711 A | 10/1996 | Yerich et al. | 607/17 |
| 5,591,215 A | 1/1997 | Greenhut et al. | 607/14 |
| 5,690,681 A | 11/1997 | Geddes et al. | 607/2 |
| 5,713,928 A | 2/1998 | Bonnet et al. | 607/9 |
| 5,713,929 A | 2/1998 | Hess et al. | 607/14 |
| 5,741,310 A | 4/1998 | Wittkampf | 607/14 |
| 5,792,193 A | 8/1998 | Stoop | 607/14 |
| 5,814,085 A | 9/1998 | Hill | 607/14 |
| 5,846,263 A | 12/1998 | Peterson et al. | 607/14 |
| 5,893,882 A | 4/1999 | Peterson et al. | 607/14 |
| 5,931,856 A | 8/1999 | Bouhour et al. | 607/9 |

* cited by examiner

REGULARIZATION OF VENTRICULAR RATE DURING ATRIAL TACHYARRHYTHMIA

This patent application claims the benefit of U.S. Provisional Application No. 60/113,988 filed Dec. 28, 1998.

FIELD OF THE INVENTION

This invention relates to the field of external and implantable cardiac pacing systems incorporated into cardiac pacemakers or implantable cardioverter/defibrillators (ICDs), particularly atrial and ventricular synchronous pacing systems, wherein ventricular heart rate is stabilized or regularized during atrial tachyarrhythmias, particularly atrial fibrillation.

BACKGROUND OF THE INVENTION

Episodes of atrial tachyarrhythmias, including atrial fibrillation (AF), are experienced by some heart patients. Although AF episodes may not be immediately life threatening, they may be associated with extreme symptoms, a reduced quality of life, and a reduced cardiac output. During AF episodes, the ventricular intervals may vary substantially from one ventricular cycle to the next if such patients have intact AV conduction. See R. J. Cohen et al., "Quantitative Model For Ventricular Response During Atrial Fibrillation", *IEEE Transactions on Biomedical Engineering* Volume 30, pages 769–782 (1983). Ventricular rate irregularity is undesirable because it is uncomfortable for the patient, may increase susceptibility to ventricular tachyarrhythmias, and can decrease cardiac output.

Many patients are not symptomatic during AF. However, symptomatic AF patients are typically treated with drugs, e.g., amiodarone, to suppress the AF and maintain sinus rhythm. These "rhythm control" drug therapies are frequently ineffectual and/or have undesirable side effects. Alternatively, physicians prescribe drugs to reduce the ventricular heart rate ("rate control"). In some patients, it is not possible to achieve rate control due to ineffective drugs, side effects, contraindications, or lack of compliance by the patient. Physicians treat patients who fail rhythm control or rate control drug therapies with AV nodal ablation and pacemaker implantation. AV node ablation is undesirable because it causes irreversible destruction of the AV node, results in the patient being pacemaker dependent, and is associated with an increased risk for sudden cardiac death.

Many dual chamber pacing systems have been proposed or clinically used to provide bradycardia pacing and respond to AF in a variety of ways to reduce patient symptoms. For example, a variety of mode switching features have been disclosed which respond to an excessively rapid atrial rhythm by causing the pacing system to switch from an atrial synchronized pacing mode, such as DDD/DDDR, to a non-synchronized mode such as VVI/VVIR or DDI/DDIR. Such mode switching features are disclosed in U.S. Pat. No. 5,144,949, by Olson, U.S. Pat. No. 5,318,594, by Limousin et al., U.S. Pat. No. 4,944,298, by Sholder, U.S. Pat. No. 5,292,340, by Crosby et al., and U.S. Pat. No. 4,932,406 by Berkovits, all incorporated herein by reference in their entireties. In such pacing systems, the primary purpose of the mode switch is to prevent the pacing system from tracking a non-physiologic atrial rate. Unfortunately, these mode switching mechanisms do not address the problem of inappropriately high, irregular ventricular rhythms that often result during AF. Ventricular pacing is commonly inhibited because the intrinsic Ventricular rate of the AF patient is commonly faster than the rate of the pacemaker.

Various ventricular pacing regimens have been proposed to attempt to stabilize or regularize the ventricular heart rate and to avoid AV nodal ablation. Wittkampf et al., ("Rate Stabilization by Right Ventricular Pacing in Patients With Atrial Fibrillation", *PACE*, Vol. 9, November–December, 1986, Part II, pp. 1147–1153 and "Effect Of Right Ventricular Pacing On Ventricular Rhythm During Atrial Fibrillation", *JACC* 11:539–545, 1988) proposed VVI pacing at a rate that results in a substantial percentage of depolarizations resulting from ventricular pacing, and a smaller percentage of depolarizations resulting from intrinsic conduction. The pacing rate was increased each time a ventricular sense event restarted the pacing escape interval and was decreased each time the pacing escape interval timed out and a ventricular pace was delivered. The articles state that this methodology provides stable ventricular rates in the presence of AF with only a moderate increase in overall ventriculiar heart rate.

Lau et al., "A New Pacing Method for Rapid Regularization and Rate Control in Atrial Fibrillation", *Am Journal of Cardiology*, Vol. 65, pp. 1198–1203, May 15, 1990 attempted to stabilize the ventricular heart rate by triggering a ventricular pace after every ventricular sense. The average triggered pacing interval was about 230 ms. It is believed that this approach doesn't effectively smooth out the ventricular rate and that it may be proarrhythmic in that the ventricular pace pulse may be delivered during the vulnerable period of ventricular repolarization.

Other DDD/DDDR pacing systems have been proposed that undergo mode switching in response to detected AF and attempt to stabilize the ventricular heart rate. Such pacing systems are disclosed in U.S. Pat. Nos. 5,480,413 and 5,591,215, both issued to Greenhut et al., and in U.S. Pat. No. 5,893,882 issued to Peterson et al., all incorporated herein by reference, which detect the presence of atrial tachyarrhythmia and switch from a dual chamber DDD/DDDR pacing mode or a VDD/VDDR pacing mode to a DDI/DDIR or VDI/VDIR pacing mode that effectively monitors the AF condition while pacing in the ventricle. In the '413 and '215 patents, the intrinsic ventricular heart rate irregularity is measured, and ventricular pacing rate is incremented and decremented based on the measured irregularity. However, pacing rate adjustments based on rate irregularity criteria require the time and energy consuming process of measuring the irregularity. The irregularity criterion also requires programming to set an appropriate target and an inappropriate irregularity criterion may result in ineffective pacing therapy. In the '882 patent, upon mode switching in response to detected AF, the ventricular pacing rate is modulated based upon preceding ventricular intervals such that the current pacing interval is set equal to the preceding intrinsic or paced interval, with an increment if the preceding interval is less than the desired or target pacing interval, as typically will be the case, or with a decrement if the preceding interval is greater than the desired pacing interval. This approach may result in a sudden increase in pacing rate after a very fast intrinsic rate, which commonly occurs during AF.

An alternative approach that attempts to smooth the ventricular heart rate employing a physiologic rate or "phys_rate" and a "flywheel" rate is disclosed in U.S. Pat. No. 5,792,193 to Stoop, incorporated herein by reference, in the context of a DDD/DDDR mode switching pacing system. During AF, phys_rate "tracks" the average ventricular rate by incrementing a small amount when a ventricular sense occurs, and decrementing when a ventricular pace occurs. The escape pacing rate, or the flywheel rate, is set to be slightly slower than the phys_rate. If the flywheel interval associated with the flywheel rate times out, a ventricular pace is delivered. In this way, ventricular pacing occurs at a rate slightly slower than the mean rate, or phys_grate. However, depending on how quickly pacing rate is incremented after a ventricular sense, and how quickly pacing rate is decremented after a ventricular pace, this feature may result in pacing at an inappropriately fast rate. For example, if the '193 feature increases pacing rate by 2 bpm after a ventricular sense and decreases by only 0.5 bpm after a ventricular pace, the feature may inappropriately pace at the upper pacing rate during an atrial flutter with 3:2 conduction.

What the art has not yet shown is a simple system that does not require complex computations of ventricular rate irregularity and stabilizes ventricular rate without increasing mean rate inappropriately.

SUMMARY OF THE INVENTION

The objective of the present invention is to regularize heart rate while avoiding pacing at inappropriately fast rates. The Ventricular Rate Regularization (VRR) feature of the present invention accomplishes this result by adjusting pacing rate according to the pattern of the most recent series of sensed or paced ventricular events. The invention may be embodied in an implantable or external cardiac pacemaker or ICD. Preferably, the invention is embodied in a device having rate-responsive pacing capabilities and operates to adjust the pacing rate of such device as it operates in DDIR, VDIR or VVIR mode.

The invention may be embodied in a dual chamber, rate responsive, pacing system operable in either the DDD or DDDR pacing mode, which, in case of detection of atrial tachyarrhythmia, automatically switches to a DDIR pacing mode to uncouple ventricular pacing from the atrial rate and stabilizes the ventricular rate by way of the VRR feature. The invention may also be embodied in a dual chamber, rate responsive, pacing system operable in the VDD or VDDR pacing mode, which, in case of detection of atrial tachyarrhythmia, automatically switches to a VDIR pacing mode and stabilizes the ventricular rate by way of the VRR feature. In these embodiments, the device operates as described in the above-cited Olson and Berkovits patents in DDIR and VDIR modes, respectively, but the escape interval of the device corresponding to the ventricular pacing rate is modulated by the VRR feature to provide a more regular rate. For patients whose atrial tachyarrhythmias are chronic, the pacing system may be programmed to the DDIR or VVIR modes with VRR operating continuously.

The VRR feature of the present invention regularizes ventricular rate by slightly elevating the pacing rate so that greater than 50% of ventricular events are paced and less than 50% of ventricular events are sensed. Ventricular pacing rate increase and decrease decisions are based on the pattern of the most recent sensed and paced ventricular events. A programmable rate limit (VRR URL) is provided to limit the maximum ventricular pacing rate that the VRR feature will achieve.

When the VRR feature is operative in the DDIR mode, the ventricular pacing rate defined by the present invention may also be influenced by the occurrence of an atrial pacing pulse delivered in the previous V-V interval if the most recent ventricular event was a sensed event (Vs). The VRR feature in this case does not increment the ventricular pacing rate if the Vs was due to intrinsic AV conduction after an atrial pace, because doing so could create positive feedback which would drive the ventricular pacing rate to the upper rate limit. Instead, the ventricular pacing rate is preferably decremented when an atrial pace is delivered in the preceding V-V sequence ended by a Vs.

In a preferred embodiment, the ventricular pacing rate is initialized at a physiologic pacing rate determined to meet the patient's need for cardiac output, and the VRR feature makes rate increase and decrease decisions based on whether the previous two ventricular events were both sensed ventricular depolarizations or "ventricular senses" (Vs-Vs), both ventricular pacing pulses or "ventricular paces" (Vp-Vp), or a sequences of ventricular paces and senses (Vp-Vs or Vs-Vp). The VRR feature incrementally increases, maintains or decreases the ventricular pacing rate depending upon the ventricular event sequence to promote ventricular heart rate stability at the lowest possible ventricular pacing rate.

The VRR feature may also include a ventricular stability rate range (VRR Stable Range) operative in the DDIR, VDIR and VVIR pacing modes such that sensed ventricular events in this range will not increment the ventricular pacing rate when they are considered to be stable. The current V-V cycle length terminated by a ventricular sensed event is measured. No increments, and preferably no changes whatsoever are made to the ventricular pacing rate if the current V-V cycle length is within the stable range, as calculated based upon one or more preceding V-V cycle length measurements.

Other features and attributes of the invention shall become apparent from the following description of the invention. The rhythms that are recognized and/or responded to in use of the VRR feature may comprise any of the supraventricular arrhythmia types, e.g., supraventricular tachycardias, atrial fibrillation and atrial flutter, but the invention is especially benefical in the case of patients suffering from atrial fibrillation.

BRIEF DESCRIPTION OF THE DRAWINGS

These and other advantages and features of the present invention will be more readily understood from the following detailed description of the preferred embodiments thereof, when considered in conjunction with the drawings, in which like reference numerals indicate identical structures throughout the several views, and wherein.

DETAILED DESCRIPTION OF THE PREFERRED EMBODIMENTS

Figure 1:
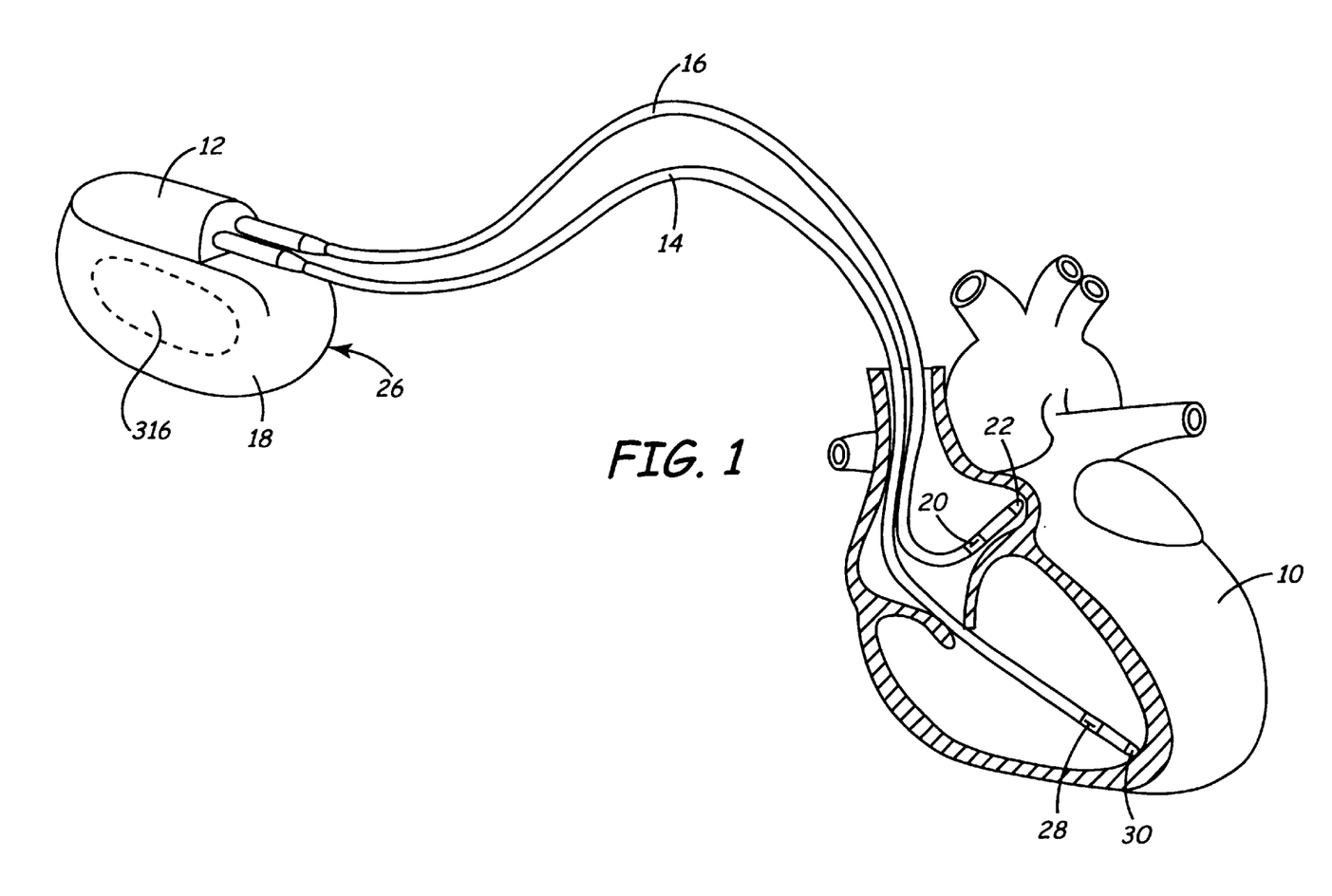
FIG. 1 is an illustration of an implantable dual chamber pacemaker according to the present invention in conjunction with an associated set of cardiac pacing leads, illustrated as located in a cutaway view of a human heart.

FIG. 1 illustrates the external configuration of a dual chamber implantable pulse generator (IPG) of a type in which the present invention may be embodied. (IPG) 26 is provided with a hermetically sealed can or housing 18, typically fabricated of bio-compatible metal such as titanium. Mounted to the top of the housing 18 is a connector block assembly 12, which receives electrical connector elements located on the proximal ends of leads 14 and 16. The IPG housing 18 can be employed as a remote indifferent pace/sense electrode referred to as the IND_CAN electrode. In this particular illustrated embodiment, a patient activity sensor 316 is mounted within the IPG housing 18 as is well known in the art. Additional or alternative physiologic sensors of the need for cardiac output experienced by the patient during exercise and rest that are well known in the art can be incorporated into the IPG 26 and/or leads 14 and 16.

Lead 16 is an atrial bipolar pacing lead, carrying two electrodes 20 and 22 that are used to both sense atrial depolarizations (P-waves) and to deliver atrial pacing (A-PACE) pulses. Atrial pacing pulses may be delivered between electrodes 20 and 22 in a bipolar pacing mode or between electrode 22 and the IND_CAN electrode in a unipolar pacing mode. Sensing of P-waves may occur between electrode 20 and electrode 22 in a bipolar sensing mode or between either of electrodes 20 and 22 and the IND_CAN electrode in a unipolar sensing mode.

Similarly, lead 14 represents a ventricular bipolar pacing lead, carrying two electrodes 28 and 30 that to are used to both sense ventricular depolarizations (R-waves) and to deliver ventricular pacing (V-PACE) pulses. Bipolar ventricular pacing may be accomplished between electrodes 30 and 28 or unipolar ventricular pacing may be accomplished between electrode 30 and the IND_CAN electrode. Sensing of ventricular depolarizations or R-waves may be accomplished between electrodes 30 and 28 in a bipolar sensing mode or between either of electrodes 30 and 28 and the IND_CAN electrode in a unipolar sensing mode. Unipolar leads may of course be substituted for the bipolar leads illustrated in this Figure.

Figure 2:
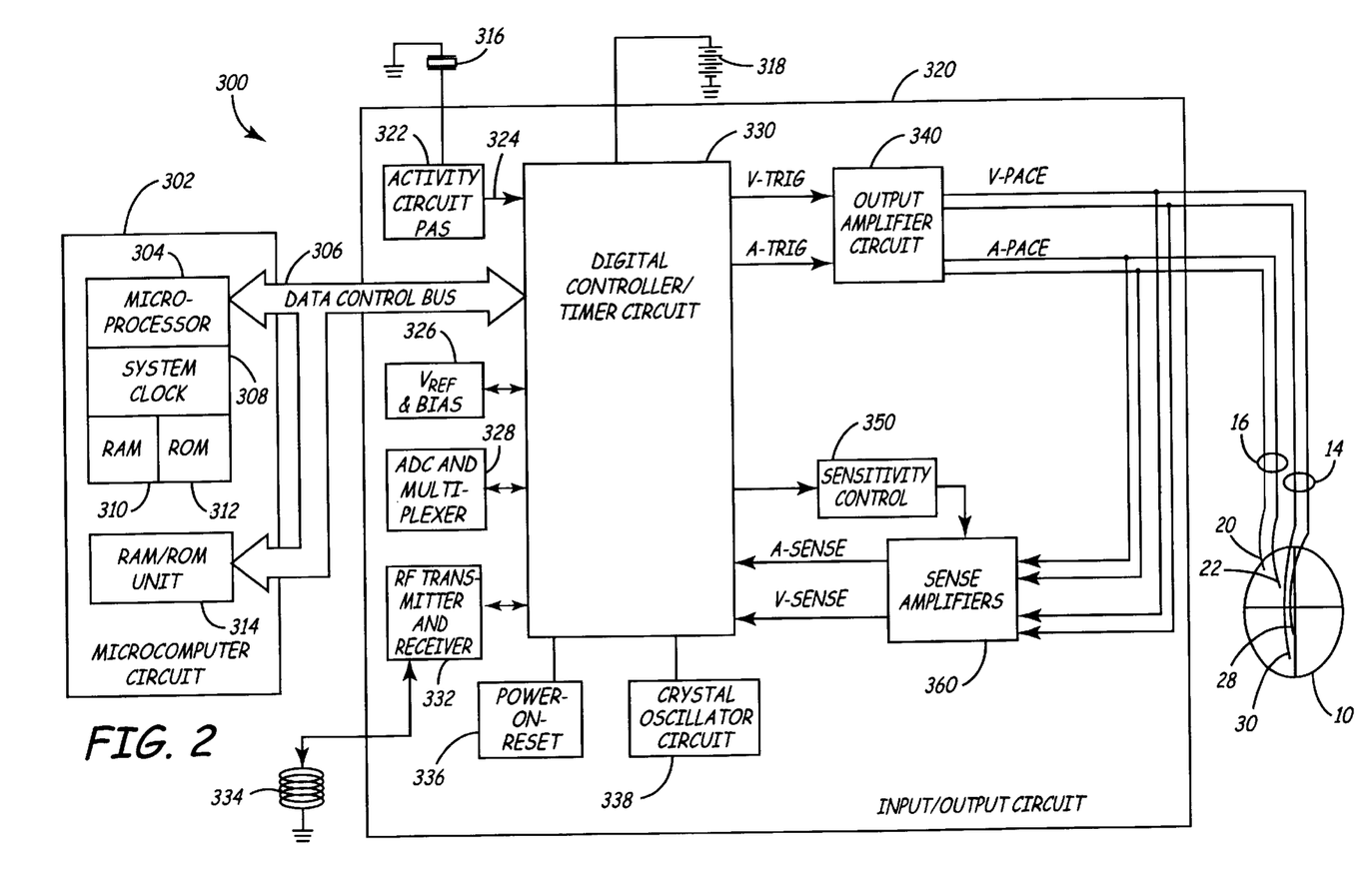
FIG. 2 is a block diagram of the dual chamber pacemaker of FIG. 1, illustrating the functional components of the pacing system.

FIG. 2 is a diagram of the circuitry within IPG 26, illustrating its interconnection with a patient's heart via ventricular lead 14 and atrial lead 16. The IPG circuit 300 is illustrated in a functional block diagram divided generally into a microcomputer circuit 302 and a pacing circuit 320. The pacing circuit 320 includes the digital controller/timer circuit 330, the output amplifiers circuit 340, and the sense amplifiers circuit 360, as well as a number of other circuits and components described below.

Crystal oscillator circuit 338 provides the basic timing clock for the pacing circuit 320, while battery 318 provides power. Power-on-reset circuit 336 responds to initial connection of the circuit to the battery for defining an initial operating condition and similarly, resets the operative state of the device in response to detection of a low battery condition. Reference mode circuit 326 generates stable voltage reference and currents for the analog circuits within the pacing circuit 320, while analog to digital converter ADC and multiplexer circuit 328 digitizes analog signals and voltage to provide real time telemetry if a cardiac signals from sense amplifiers 360, for uplink transmission via RF transmitter and receiver circuit 332. Voltage reference and bias circuit 326, ADC and multiplexer 328, power-on-reset circuit 336 and crystal oscillator circuit 338 may correspond to any of those presently used in current marketed implantable cardiac pacemakers.

Data transmission to and from the external programmer is accomplished by means of the telemetry antenna 334 and an associated RF transmitter and receiver 332, which serves both to demodulate received downlink telemetry and to transmit uplink telemetry. Uplink telemetry capabilities will typically include the ability to transmit stored digital information, e.g. operating modes and parameters, EGM histograms, and other events, as well as real time EGMs of atrial and/or ventricular electrical activity and Marker Channel pulses indicating the occurrence of sensed and paced depolarizations in the atrium and ventricle, as are well known in the pacing art. In addition, a real time clock is incorporated into the digital controller/timer circuit for a number of uses, including timing the time of day when tests, e.g., pacing and sensing threshold tests, are to be undertaken or to append a date and time stamp to event data stored in memory for later telemetry out to an external programmer.

Microcomputer 302 contains a microprocessor 304 and associated system clock 308 and on-processor RAM and ROM chips 310 and 312, respectively. In addition, microcomputer circuit 302 includes a separate RAM/ROM chip 314 to provide additional memory capacity. Microprocessor 304 normally operates in a reduced power consumption mode and is interrupt driven. In one embodiment of the invention, microprocessor 304 is a custom microprocessor adapted to fetch and execute instructions stored in RAM/ROM unit 314 in a conventional manner. Microprocessor 304 is awakened in response to defined interrupt events, which may include A-TRIG and V-TRIG signals generated by timers in digital timer/controller circuit 330 and A-SENSE and V-SENSE signals generated by sense amplifier circuit 360, among others. The specific values of the intervals and delays timed out by digital controller/timer circuit 330 are controlled by the microcomputer circuit 302 by means of data and control bus 306 from programmed-in parameter values and operating modes. Digital controller/timer circuit 330 includes a set of timers and associated logic circuits for timing intervals associated with any of the above-discussed pacing modes available in the device, including discharge/recharge intervals, measured intervals between paced and sensed atrial and ventricular events, pacing escape intervals, including A-A, A-V, V-A, and/or A-V escape intervals and upper rate intervals. The included timers also time out other periods and intervals employed in the available pacing modes, including the post-ventricular atrial refractory period (PVARP), post-ventricular atrial blanking period (PVABP), ventricular blanking period (VBP), and ventricular refractory period (VRP), atrial refractory period (ARP) and atrial blanking period (ABP), as is conventional in devices of this type.

Microcomputer 302 controls the operational functions of digital controller/timer circuit 330, specifying which of the above-listed timing intervals are employed, and setting the programmed-in base timing intervals, via data and control bus 306. Digital controller/timer circuit 330 starts and times out these intervals and delays for controlling operation of the atrial and ventricular sense amplifiers in sense amplifiers circuit 360 and the atrial and ventricular pace pulse generators in output amplifiers circuit 340. The microprocessor also processes the information discussed below in conjunction with FIGS. 4A and 4B to derive the pacing rates provided by the VRR feature of the present invention.

The output amplifier circuit 340 contains atrial and ventricular pacing pulse generators corresponding to any of those presently employed in commercially marketed cardiac pacemakers providing atrial and ventricular pacing. In order to trigger generation of a V-PACE pulse, digital controller/timer circuit 330 generates a V-TRIG signal. Similarly, digital controller/timer circuit 330 generates an A-TRIG signal in order to trigger delivery of the A-PACE pulse. The output amplifiers circuit 340 includes switching circuits for coupling selected pace/sense electrode pairs from among the atrial and ventricular leads 14 and 16 and the IND_CAN electrode to the atrial and ventricular pulse generators so as to provide bipolar or unipolar atrial and/or ventricular pacing.

The sense amplifier circuit 360 contains sense amplifiers corresponding to any of those presently employed in commercially marketed cardiac pacemakers for sensing of atrial and ventricular depolarizations. Digital controller/timer circuit 330 provides programmed sensitivity commands to the sensitivity control register 350 that control sensitivity settings of the atrial and ventricular sense amplifiers 360. The sense amplifier circuit 360 also includes switching circuits for coupling selected atrial and ventricular lead conductors and the IND_CAN electrode to the atrial and ventricular sense amplifiers for atrial and/or ventricular bipolar or unipolar sensing. The sense amplifiers circuit 360 further includes blanking circuits for uncoupling the selected pairs of the lead conductors and the IND_CAN electrode from the inputs of the atrial and ventricular sense amplifiers during the ABP, PVABP and VBP before, during, and after delivery of a pacing pulse to any of the pace/sense electrode pairs to avoid saturation of the sense amplifiers.

If the IPG is programmed to a rate responsive mode, e.g. DDDR, DDIR, or VDIR, the signals output by one or more physiologic sensors are employed to provide pacing at a rate sufficient to meet the patient's need for cardiac output. Many physiologic sensors and/or signals have been employed in the prior art alone or in combination for measuring one or more rate control parameter (RCP) which directly or indirectly relate to metabolic requirements (e.g., demand for oxygenated blood). Such RCPs include, for example, QT interval evoked response, physical activity of the body, right ventricular blood pressure and the change of right ventricular blood pressure over time, venous blood temperature, venous blood oxygen saturation, respiration rate, minute ventilation, and various pre and post-systolic time intervals measured by impedance or pressure sensing within the right ventricle of the heart. Such RCP-measuring, sensor-driven pacemakers have been developed for the purpose of restoring rate response to exercise or other physiological stresses in patients lacking the ability to increase rate adequately by exertion. The uses of these RCPs alone or in combination are disclosed, for example, in commonly assigned, U.S. Pat. No. 5,562,711 issued to Yerich et al., and U.S. Pat. No. 5,282,839 issued to Roil et al., both incorporated herein by reference. Any one or more of such RCPs and features using the same to derive a pacing rate in the rate responsive pacing modes employed in the present invention can be employed.

For simplicity of discussion, in the exemplary IPG circuit 300, the RCP is the output signal of the patient activity sensor 316 processed in the patient activity sensor (PAS) circuit 322 to derive a physiologic escape interval and corresponding PAS_RATE. A timed interrupt, e.g., every two seconds, may be provided in order to allow the microprocessor 304 to analyze the output of the PAS circuit 322 and update the PAS_RATE defined escape interval employed to define the pacing rate. (e.g. A-A or V-V escape intervals). The microprocessor 304 also optionally calculates A-V delays, post-ventricular time periods, and post-atrial time periods, which vary with the physiologic escape interval, established in response to the RCP(s) and/or with the intrinsic atrial rate. As discussed below, the PAS_RATE plays a role in establishing the VRR_RATE while the VRR feature is operative during DDIR, VDIR or VVIR pacing.

The illustrated IPG block diagram of FIG. 2 is merely exemplary, and corresponds to the general functional organization of most multi-programmable microprocessor controlled DDDR cardiac pacemakers or cardiac pacing systems embodied into ICDs presently commercially available. It is believed that the present invention is most readily practiced in the context of such a pacing system, and that the present invention can therefore readily be practiced using the basic hardware of existing microprocessor controlled dual chamber pacing systems, as presently available, with the invention implemented primarily by means of modifications to the software or firmware stored in the ROM 312 and with certain hardware logic and timing circuitry described above. However, the present invention may also be usefully practiced by means of a full custom integrated circuit, for example, a circuit taking the form of a state machine, in which a state counter serves to control an arithmetic logic unit to perform calculations according to a prescribed sequence of counter controlled steps. As such, the present invention should not be understood to be limited to a pacing system having an architecture as illustrated in FIG. 2, and a circuit architecture as illustrated in FIG. 2 is not believed to be a prerequisite to employing the VRR feature of the present invention.

Figure 3:
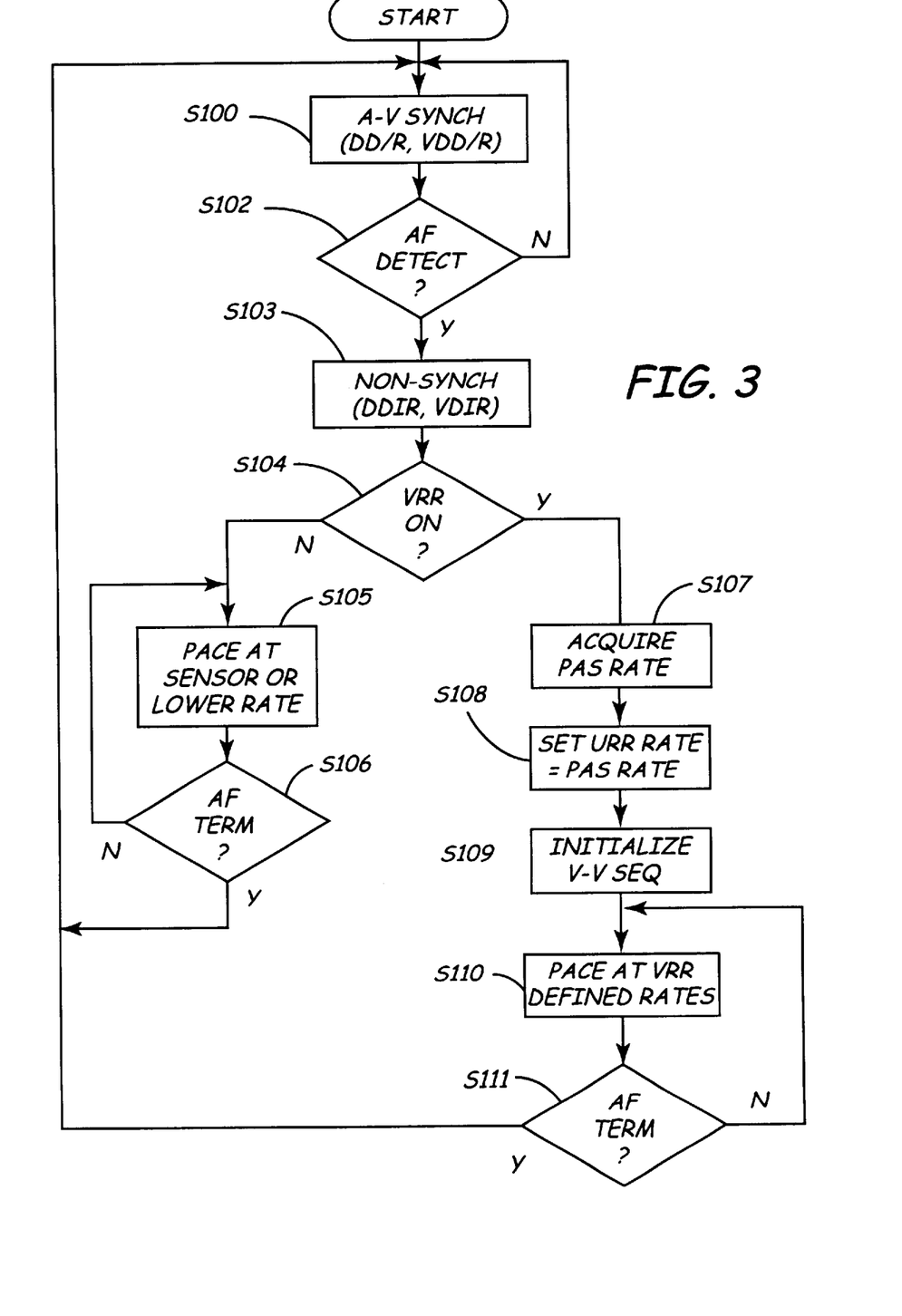
FIG. 3 is a flow chart illustrating the general operation of mode switching from DDD/R or VVD/R to DDIR or VDIR response to detected supraventricular tachyarrhythmia in a dual chamber pacemaker embodying the present invention.

FIG. 3 is a functional flow chart illustrating the over-all operation of a device according to the present invention, in which mode switching from an atrial synchronous mode (e.g. DDD, DDDR, VDD, VDDR) to a non-synchronous mode (e.g. DDIR, VDIR) is provided. The VRR feature is activated during non-synchronous pacing.

The device normally operates in an atrial synchronous mode, indicated at S100, during which the microprocessor 304 (FIG. 2) checks at S102 to determine whether a supraventricular tachyarrhythmia such as atrial fibrillation is underway. If so, the microprocessor changes the pacing mode to a non-synchronous mode at S103.

Any of the numerous known methods of detection of atrial tachyarrhythmias may be employed in anti-tachyarrhythmia pacemakers and ICDs, including those disclosed in patents cited above, may be employed in the context of the present invention to trigger a switch to a non-synchronous mode. Similarly, any of the high atrial rate criteria that have been published and/or used clinically to effect mode switching in DDD/DDDR pacing systems, including those disclosed in patents cited above may also be employed in the practice of the present invention.

If a mode switch is made at S103 and VRR is programmed "ON" as determined in step S104, the present value of the sensor indicated pacing rate (PAS) is acquired at S107. The VRR specified pacing rate parameter (VRR RATE) is initialized and set equal to the PAS RATE at S108. Thereafter, during non-synchronous pacing, information regarding the preceding V-V sequence is updated and stored in a portion of RAM 30 (FIG. 2) referred to hereafter as the V_EVENTS buffer after each ventricular sensed event or ventricular paced event. In some embodiments, all sensed ventricular events may be employed to define the V-V sequences. In other embodiments, only non-refractory sensed ventricular events might be employed. Information stored in the V_EVENTS buffer includes the types of ventricular events (sensed depolarizations or delivered pacing pulses) that initiated and ended the V-V sequence. The heart rate corresponding to the V-V cycle is also stored for use in assessing the stability of the ventricular rate as discussed below. In the DDIR mode (if entered at S103), flags (Ap FLAG) indicative of delivery of atrial pacing pulses during the V-V sequences may also be stored. The PAS RATE is employed as the effective pacing rate at S108 until a sequence of two ventricular events (V-V sequence)

can be acquired at S109. Any Ap FLAGs occurring during the acquired V-V sequence are also retained. Thereafter at S110 the device paces in the non-synchronous mode (DDIR, VDIR) at ventricular pacing rates controlled by the VRR feature. Control of pacing rates by the VRR feature is described in more detail in conjunction with FIGS. 4A and 4B.

The device continues to pace in the non-synchronous mode until detection of termination of the atrial tachyarrhythmia at S111, after which the device returns to pacing in an atrial synchronous mode at S100. Any of the AF reversion criteria that have been published and/or used clinically to effect mode switching in dual chamber pacing systems, including those disclosed in the patents cited above, may also be employed in the practice of step S111. In the event that the VRR feature is turned off at S104, the device paces in a conventional manner in the non-synchronous mode at S105, until detection of termination of the atrial tachyarrhythmia at S106.

As noted above, the invention may also be practiced in a device that is permanently programmed to a non-synchronous mode (e.g. VVIR, DDIR). In such a device the VRR feature may be continually activated, as noted above. In alternative embodiments, the VRR feature may be activated in response to supraventricular tachyarrhyhthmias detected while pacing in a non-synchronous mode and may be deactivated in response to detection of termination of the tachyarrhtmia.

Figure 4A:
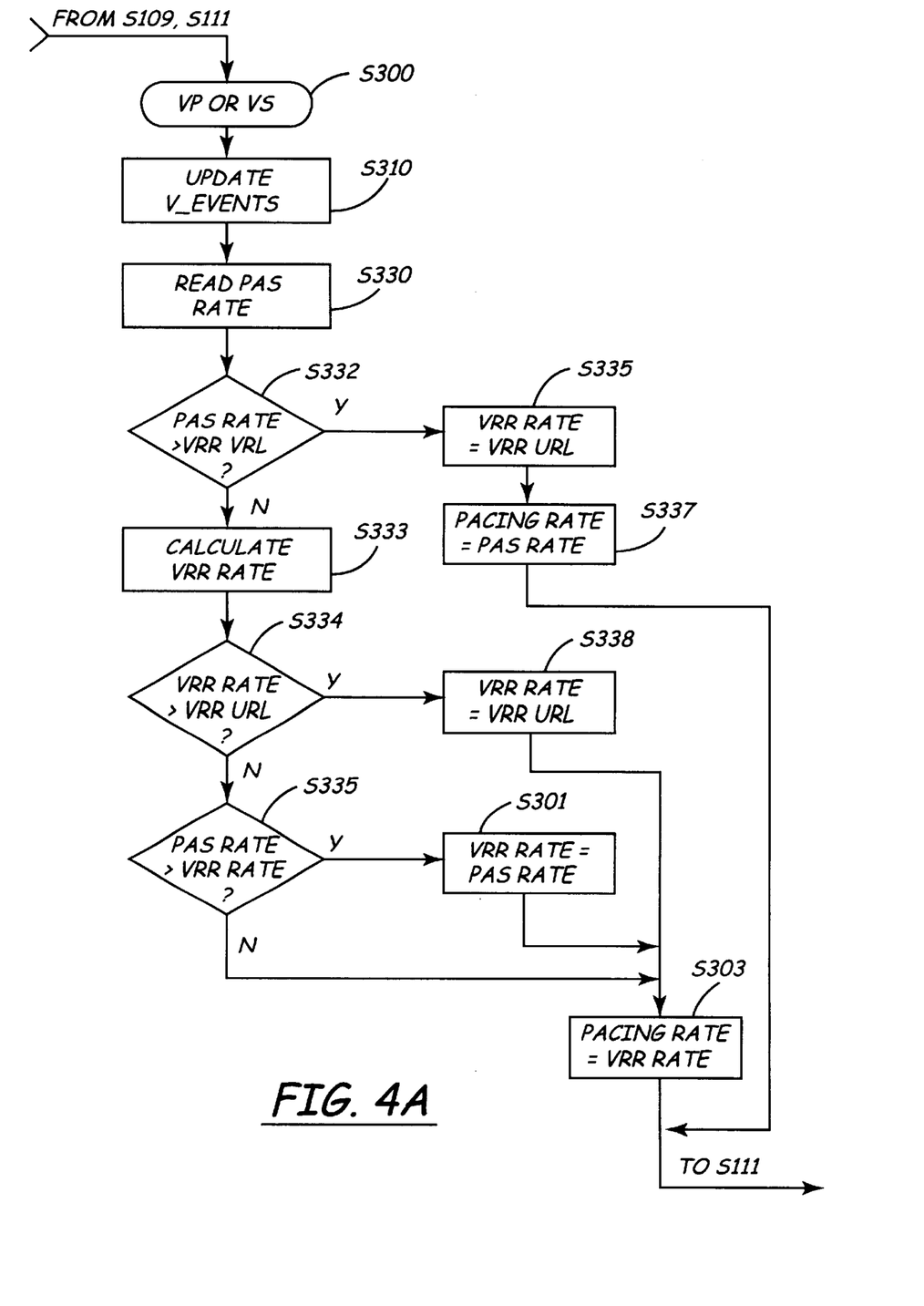
FIGS. 4A and 4B are a flow chart illustrating the VRR feature of the present invention in the DDIR or VDIR pacing mode.
Figure 4B:
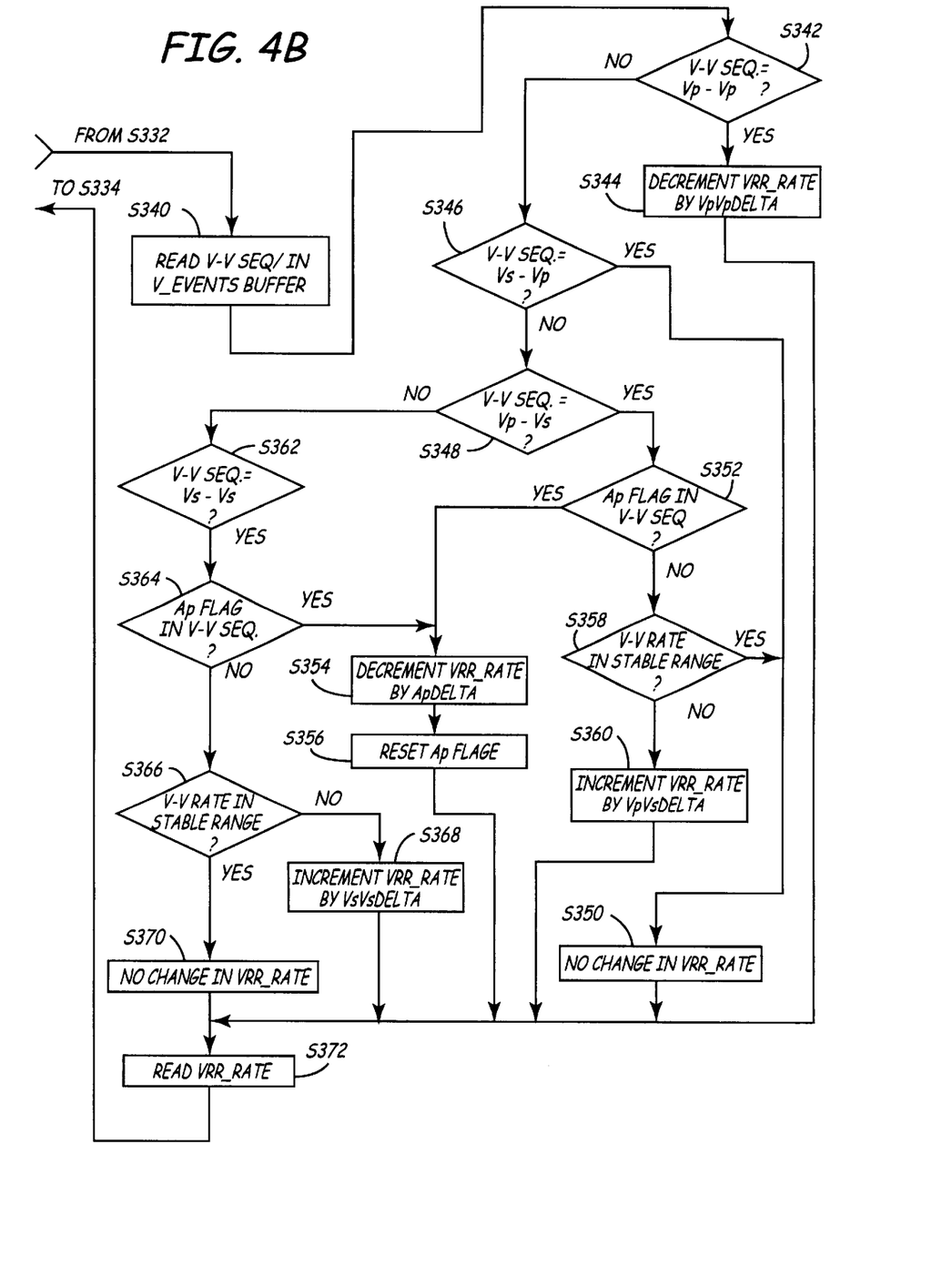

FIGS. 4A and 4B are functional flow charts illustrating basic operational characteristics of the VRR feature of the present invention, illustrating the mechanism by which the invention selects the ventricular pacing rate following a sensed or paced ventricular event. These flow charts apply to the operation of the device in DDIR, VDIR or VVIR modes.

In the following discussion, the operation of the device is often described in terms of "rates". In typical embodiments, timing operations within the pacemaker will be often be accomplished by calculating and timing escape intervals corresponding to the described rates. Modulation of the pacing rate according to the VRR feature should thus be understood to be accomplished either by modulation of either a rate or of a corresponding escape interval. Values expressed as rates and the intervals corresponding to the expressed rates should be understood to be equivalent.

In conjunction with both FIGS. 4A and 4B it should also be understood that control of the ventricular pacing rate in dual chamber pacemakers embodying the present invention may be accomplished using either atrial based timing (e.g. A-A escape intervals in conjunction with A-V escape intervals), ventricular based timing (e.g. V-V escape intervals) or other timing schemes. Regardless of which timing scheme is present in the device, the VRR feature operates to modify the appropriate device defined escape interval that regulates the ventricular pacing rate.

Responsive to the occurrence of a paced or sensed ventricular event at 300, the V_EVENTS buffer is updated at 310. Any Ap FLAGs previously set during the V-V sequence are retained and employed as described below. At S330, the present value of the PAS rate is acquired and it is compared to a programmed VRR upper rate limit (VRR URL) at S332. VRR URL is preferably less than the maximum allowable value for PAS RATE (Upper Sensor Rate), so that the sensor indicated pacing rate may exceed the maximum value of VRR RATE. If PAS RATE is greater than VRR URL, VRR RATE is set equal to VRR URL and the PAS RATE is employed to define the ventricular pacing escape interval at S337. If PAS RATE is less than or equal to VRR URL, the microprocessor at S333 calculates a new value of VRR RATE based upon the preceding stored V-V sequence, the preceding value of VRR RATE and other factors as discussed in more detail below in conjunction with FIG. 4B.

At S334 the microprocessor compares the value of VRR RATE calculated at S333 with VRR URL. If VRR RATE is greater than VRR URL, VRR RATE is set equal to VRR URL at S338 and the newly defined VRR RATE is used to define the ventricular pacing escape interval at S303. If VRR RATE is less than or equal to VRR URL, at S336 the microprocessor compares the current value of PAS RATE with the value of VRR RATE calculated at S333. If PAS RATE is greater than VRR RATE, VRR RATE is set equal to PAS RATE and the newly defined VRR RATE is used to define the ventricular pacing escape interval at S303. If PAS RATE as calculated at S333 is less than or equal to VRR RATE, VRR RATE is un-altered and is used to define the ventricular pacing escape interval at S303.

FIG. 4B is a functional flow chart illustrating the mechanism by which the microprocessor calculates the value of VRR RATE at S333. In conjunction with this Figure, it should be kept in mind that in the VVIR or VDIR pacing mode, there is no atrial pacing, so the Ap FLAG will never be set. In the preferred embodiment, as described, the pacemaker employs V-V timing.

In step S340, the V-V sequence in the V_EVENTS buffer is read, and adjustments to VRR_RATE are made in the steps S342–S372 as follows:

Vp-Vp: If the last two ventricular events were both V-PACEs (Vp-Vp) as determined in step S342, the VRR_RATE is decreased by the VpVpΔ value (1 bpm nominally) in step S344.

Vs-Vp: The VRR_RATE is changed by a VsVpΔ value (0 bpm nominally) in step S350 if the last ventricular event was a V-PACE and the previous ventricular event was a V-SENSE (Vs-Vp) as determined in step S346.

Vp-Vs: When the last ventricular event was a V-SENSE and the previous ventricular event was a V-PACE (Vp-Vs) as determined in step S348, one of three adjustments may be made:

The VRR_RATE is not incremented and is preferably decreased by the ApΔ value (1 bpm nominally) in step S354 if the pacing mode is DDIR and the Ap FLAG was set in the previous V-V sequence; or No increment to and preferably no change in VRR_ RATE is made in step S350 if the current ventricular heart rate derived from the V-V interval ending with a V-SENSE is within the VRR Stable Range (nominally within 5 bpm of the current VRR_RATE) as determined in step S358; or The VRR_RATE is increased by the VpVsΔ value (1 bpm nominally) in step S360 if the current ventricular heart rate derived from the V-V interval ending with a V-SENSE in step S300 of FIG. 4A is not within the VRR Stable Range as determined in step S358.

Vs-Vs: When the last two ventricular events were both V-SENSEs (Vs-Vs) as determined in step S362, one of three adjustments may be made:

The VRR_RATE is not incremented and preferably is decreased by the ApΔ value (1 bpm nominally) in step S354 if the pacing mode is DDIR and the Ap FLAG was set in the previous V-V cycle as determined in step S364; or No increment to and preferably change in VRR_RATE is made in step S370 if the current ventricular heart rate derived from the V-V sequence ending with a V-SENSE in step S300 of FIG. 4A is within the VRR Stable Range (nominally within 5 bpm of the current VRR_RATE) as determined in step S366; or The VRR_RATE is increased by the VsVsΔ value (1 bpm nominally) in step S368 if the current ventricular heart rate derived from the V-V interval ending with a V-SENSE in step S300 of FIG. 4A is not within the VRR Stable Range as determined in step S366.

The resulting VRR_RATE from one of steps S344, S350, S354, S360, S368 and S370 is read in step S372 and compared to VRR_URL and PAS_RATE in steps S334 and S336 of FIG. 4A, as discussed above. The Ap FLAG is reset in step S356 when the VRR_RATE is decremented in step S354, to prepare for the next VRR processing cycle.

The incremental changes to VRR_RATE in response to the Vs and Vp cardiac events are programmable. The nominal increment and decrement variables are presented in the following Table I. Increment and decrement values may be defined in terms of beats per minute or in terms of time intervals, as noted above.

TABLE I

| Parameter Name | Description | Nominal (bpm) |
| --- | --- | --- |
| VpVpΔ | Change in VRR pacing rate after a Vp-Vp sequence | −1 |
| VsVpΔ | Change in VRR pacing rate after a Vs-Vp sequence | 0 |
| VpVsΔ | Change in VRR pacing rate after a Vp-Vs sequence | 1 |
| VsVsΔ | Change in VRR pacing rate after a Vs-Vs sequence | 2 |
| ApΔ | Change in VRR pacing rate after an Ap | −1 |
| VRR Stable Range | Rate tolerance window w/in which rates considered "stable" | 5 |
| VRR_URL | Fastest VRR pacing rate (bounded by Upper Sensor Rate as (USR-10 bpm). | 120 or USR −10 (which ever is less) |

Figure 5:
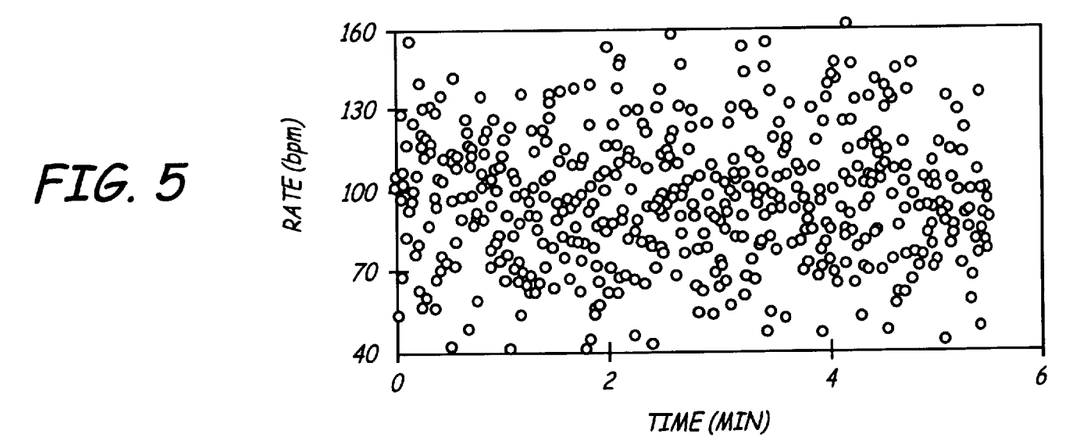
FIG. 5 is a chart illustrating the irregularity of the ventricular rate of a heart during AF.
Figure 6:
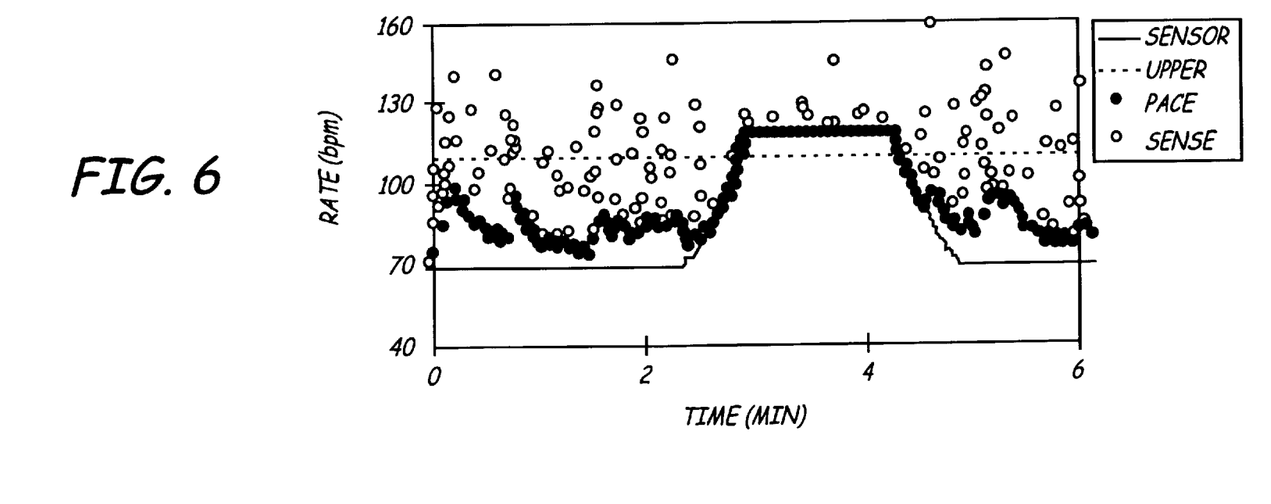
FIG. 6 is a chart illustrating the effect of ventricular pacing employing the VRR feature of the present invention during AF.

FIG. 5 is a ventricular rate trend illustrating the irregularity of the ventricular rate of a heart during an AF episode. FIG. 6 is a chart illustrating the effect of ventricular pacing employing the VRR feature of the present invention during an AF episode. Ventricular heart rate is substantially regularized as shown in FIG. 6. FIG. 6 also illustrates the scenario when PAS RATE exceeds the VRR URL.

While the above described embodiments employ a two event, V-V sequence, it will be understood that the V-V sequence may comprise "N" Vs and Vp events, where N>1 and there are $2^N$ possible sequences. When N=2, there are four event sequences and four incremental rate changes described above. When N=3, there are eight possible V-V-V event sequences comprising Vs-Vs-Vs, Vs-Vs-Vp, Vs-Vp-Vp, Vs-Vp-Vs, Vp-Vs-Vs, Vp-Vs-Vp, Vp-Vp-Vs, and Vp-Vp-Vp. Incremental VRR changes can be ascribed to each sequence, and the occurrence of an A-PACE and ventricular rate stability can be taken into account in a like manner to steps S348–S370 of FIG. 4B for those four sequences ending with a Vs in this V-V-V example.

The particular VRR_RATE changes are expressed above as constituting "Δ" increments or decrements of a current VRR_RATE employed to derive or calculate a new VRR_RATE to be used in the next ventricular pacing cycle. It will be understood that a set of all possible VRR_RATEs may be stored in memory and that a particular VRR_RATE is retrieved from memory depending upon the current VRR_RATE and the rate change deemed necessary following the VRR feature.

It will also be understood that whenever the VRR feature is entered in step S107, the VRR_RATE changes and other data, e.g., atrial rate, Ap events, ventricular rate regularity determinations, PAS_RATE, etc., may be stored in RAM 310 (FIG. 2) for retrieval via an uplink telemetry interrogation command for display by a programmer and analysis by the clinician. Displays, e.g., FIGS. 5 and 6 may be provided by the programmer to assist in visualization of the VRR mode during the AF episode.

The present invention may also be of use in multi-chamber pacing systems providing pacing and sensing in both the right and left ventricles. The present invention may also be of use with pacing systems for pacing at specific ventricular pacing sites, e.g., the right ventricular outflow tract (RVOT) or the bundle of His.

It will be understood that certain of the above-described structures, functions and operations of the pacing systems of the preferred embodiments are not necessary to practice the present invention and are included in the description simply for completeness of an exemplary embodiment or embodiments. It will also be understood that there may be other structures, functions and operations ancillary to the typical operation of such pacing systems that are not disclosed and are not necessary to the practice of the present invention. In addition, it will be understood that specifically described structures, functions and operations set forth in the above-listed, commonly assigned and co-pending patent applications can be practiced in conjunction with the present invention, but they are not essential to its practice.

The above specification and the embodiments disclosed are intended to allow one of skill in the art to incorporate the present invention into a modern implantable cardiac pacing system of a cardiac pacemaker or ICD. However, it is of course understood that the particular implementation of the invention will vary depending upon the particular underlying circuitry types and software systems employed. In the following claims, means-plus-function clauses are intended to cover the structures described herein as performing the recited function and not only structural equivalents but also equivalent structures. The above disclosure should be considered exemplary, rather than limiting with regard to the claims that follow.

In conjunction with the above disclosure, we claim:

1. A pacing system for pacing a patient's heart during a supraventricular arrhythmia comprising:
    means for sensing ventricular depolarizations;
    pulse generation means for timing a ventricular rate regularization escape interval from a sensed ventricular depolarization or a previously delivered ventricular pacing pulse, and for providing ventricular pacing pulses to a ventricle of the heart in a ventricular rate regularization mode at a ventricular rate regularization pacing rate wherein a ventricular pacing pulse is delivered upon expiration of the ventricular rate regularization escape interval;
    means for retaining a ventricular event sequence of at least two previous ventricular events, each of said events being one of a ventricular pacing pulse and a sensed ventricular depolarization; and
    regularization means for establishing said ventricular rate regularization pacing rate according to the pattern of events included in the ventricular event sequence.

2. The pacing system of claim 1, further comprising:
    means for establishing a physiologic ventricular heart rate related to the patient's need for cardiac output; and
    the regularizing means further comprises means for establishing the ventricular rate regularization pacing rate as a function of physiologic ventricular heart rate and a preceding ventricular event sequence.

3. The pacing system of claim 2, wherein if said retaining means retains a ventricular event sequence comprising a ventricular pace preceded by a ventricular pace, the regularizing means responds by establishing said ventricular rate regularization pacing rate as a function of the physiologic ventricular heart rate and the preceding ventricular event sequence.

4. The pacing system of claim 1 or claim 2, wherein if the retaining means retains a ventricular event sequence comprising a ventricular pacing pulse preceded by a ventricular pacing pulse, the regularizing means responds by decrementing the ventricular rate regularization pacing rate.

5. The pacing system of claim 1 or claim 2, wherein if the retaining means retains a ventricular event sequence comprising a ventricular pacing pulse preceded by a sensed ventricular depolarization, the regularizing means responds by not increasing the ventricular rate regularization pacing rate.

6. The pacing system of claim 1 or claim 2, further comprising:
  means for detecting atrial depolarizations;
  means for providing atrial pacing pulses to an atrium of the heart during said ventricular rate regularization escape interval in the absence of detected atrial depolarizations, whereby atrial pacing pulses may occur within ventricular event sequences; and
  wherein if said retaining means retains a ventricular event sequence comprising a sensed ventricular depolarization preceded by a ventricular pacing pulse and an atrial pacing pulse was delivered within the retained ventricular event sequence, the regularizing means responds by not incrementing the ventricular rate regularization pacing rate.

7. The pacing system of claim 1 or claim 2, wherein:
  the regularizing means further comprises ventricular stability determining means for determining if a ventricular event sequence comprising a sensed ventricular depolarization preceded by a ventricular pacing pulse is within a stable range; and
  wherein if said retaining means retains a ventricular event sequence within the stable range, the ventricular event sequence comprising a sensed ventricular depolarization preceded by a ventricular pacing pulse, the regularizing means responds by not incrementing the ventricular rate regularization pacing rate; and
  wherein if said retaining means retains a ventricular event sequence outside the stable range, comprising a sensed ventricular depolarization preceded by a ventricular pacing pulse, the regularizing means responds by incrementing the ventricular rate regularization pacing rate.

8. The pacing system of claim 1 or claim 2, further comprising:
  means for detecting atrial depolarizations;
  means for providing atrial pacing pulses to an atrium of the heart during said ventricular rate regularization escape interval in the absence of a detected atrial depolarization, whereby atrial pacing pulse may occur within the ventricular event sequences; and
  wherein if the retaining means retains a ventricular event sequence comprising a sensed ventricular depolarization preceded by a sensed ventricular depolarization and an atrial pace was delivered within the retained ventricular event sequence, the regularizing means responds by not incrementing the ventricular rate regularization pacing rate.

9. The pacing system of claim 1 or claim 2, wherein:
  the regularizing means further comprises ventricular stability determining means for determining if a ventricular event sequence comprising a sensed ventricular depolarization preceded by a sensed ventricular depolarization has a rate within a stable range; and
  wherein if said retaining means retains a ventricular event sequence comprising a sensed ventricular depolarization preceded by a sensed ventricular depolarization and having a rate within the stable range, the regularizing means responds by not incrementing said ventricular rate regularization pacing rate; and
  wherein if said retaining means retains a ventricular event sequence comprising a sensed ventricular depolarization preceded by a sensed ventricular depolarization and having a rate outside the stable range, the regularizing means responds by incrementing said ventricular rate regularization pacing rate.

10. The pacing system of claim 1 or claim 2, further comprising:
  means for detecting the onset of heart rhythms consistent with a supraventricular arrhythmia; and
  means responsive to detection of said heart rhythms for initiating operation of the pulse generation means in said ventricular rate regularization pacing mode.

11. A method of pacing a patient's heart during a supraventricular arrhythmia comprising the steps of:
  detecting ventricular depolarizations;
  providing ventricular pacing pulses to a ventricle of the heart in a ventricular rate regularization mode at a ventricular rate regularization pacing rate such that a ventricular pacing pulse is delivered upon expiration of a ventricular rate regularization escape interval timed from a sensed ventricular depolarization or a previously delivered ventricular pacing pulse;
  retaining a ventricular event sequence of recent ventricular events, each of said events being one of a ventricular pacing pulse and a sensed ventricular depolarization; and
  establishing said ventricular rate regularization pacing rate according to the pattern of events included in the ventricular event sequence.

12. The pacing method of claim 11, further comprising the step of:
  establishing a physiologic ventricular heart rate related to the patient's need for cardiac output; and
  wherein establishing the ventricular rate regularization pacing rate comprises establishing the ventricular rate regularization pacing rate as a function of both said physiologic ventricular heart rate and the ventricular event sequence.

13. The pacing method of claim 12, wherein, if retaining a ventricular event sequence comprises retaining a ventricular event sequence comprising a ventricular pacing pulse preceded by a ventricular pacing pulse, establishing the ventricular rate regularization pacing rate comprises changing said ventricular rate regularization pacing rate established as a function of the physiologic ventricular heart rate and a preceding ventricular event sequence.

14. The pacing method of claim 11 or claim 12, wherein if retaining a ventricular event sequence comprises retaining a ventricular event sequence comprising a ventricular pacing pulse preceded by a ventricular pacing pulse, establishing the ventricular rate regularization pacing rate comprises not incrementing said ventricular rate regularization pacing rate.

15. The pacing method of claim 11 or claim 12, wherein:

if retaining a ventricular event sequence comprises retaining a ventricular event sequence comprising a ventricular pacing pulse preceded by a sensed ventricular depolarization, establishing the ventricular rate regularization pacing rate comprises not incrementing said ventricular rate regularization pacing rate.

16. The pacing method of claim 11 or claim 12, further comprising the steps of:

detecting atrial depolarizations;

providing atrial pacing pulses to an atrium of the heart during the ventricular rate regularization escape intervals in the absence of sensed atrial depolarizations, whereby said atrial pacing pulses may occur within said ventricular event sequences; and wherein if retaining a ventricular event sequence comprises retaining a ventricular event sequence comprising a sensed ventricular depolarization preceded by a ventricular pacing pulse and an atrial pace was delivered within the retained ventricular event sequence, establishing the ventricular rate regularization pacing rate comprises not incrementing said ventricular rate regularization pacing rate.

17. The pacing method of claim 11 or claim 12, wherein:

establishing the ventricular rate regularization pacing rate further comprises the determining if a ventricular event sequence comprising a sensed ventricular depolarization preceded by a ventricular pacing pulse has a rate within a stable range; and wherein, if retaining a ventricular event sequence comprises retaining a ventricular event sequence comprising a sensed ventricular depolarization preceded by a ventricular pacing pulse and having a rate within the stable range, establishing the ventricular rate regularization pacing rate comprises not incrementing said ventricular rate regularization pacing rate; and wherein, if retaining a ventricular event sequence comprises retaining a ventricular event sequence comprising a sensed ventricular depolarization preceded by a ventricular pacing pulse and having a rate outside the stable range, establishing the ventricular rate regularization pacing rate comprises incrementing the ventricular rate regularization pacing rate.

18. The pacing method of claim 11 or claim 12, further comprising the steps of:

detecting atrial depolarizations;

providing atrial pacing pulses to an atrium of the heart during said ventricular rate regularization escape intervals, whereby said atrial pacing pulses may occur within said ventricular event sequences; and:

wherein if retaining a ventricular event sequence comprises retaining a ventricular event sequence comprising a ventricular sense preceded by a ventricular sense, during which sequence an atrial pacing pulse was delivered, establishing the ventricular rate regularization pacing rate comprises not incrementing said ventricular rate regularization pacing rate.

19. The pacing method of claim 17, wherein:

establishing the ventricular rate regularization pacing rate further comprises determining if a ventricular event sequence comprising a ventricular sense preceded by a ventricular sense is within a stable range; and wherein, if retaining a ventricular event sequence comprises retaining a ventricular event sequence comprising a sensed ventricular depolarization preceded by a sensed ventricular depolarization and having a rate within the stable range, establishing the ventricular rate regularization pacing rate comprises not incrementing said ventricular rate regularization pacing rate; and wherein, if retaining a ventricular event sequence comprises retaining a ventricular event sequence comprising a sensed ventricular depolarization preceded by a sensed ventricular depolarization and having a rate outside the stable range, establishing the ventricular rate regularization pacing rate comprises incrementing said ventricular rate regularization pacing rate.

20. The pacing method of claim 11 or claim 12, further comprising:

detecting the onset of heart rhythms consistent with a supraventricular arrhythmia; and initiating operation of said ventricular rate regularization pacing mode responsive to detection of said heart rhythms.

* * * * *